(12) United States Patent
Fraley

(10) Patent No.: US 9,291,553 B2
(45) Date of Patent: Mar. 22, 2016

(54) SYSTEM AND APPARATUS FOR ANALYSIS OF A GUAYULE PLANT IN SITU

(71) Applicant: PANARIDUS, LLC, Casa Grande, AZ (US)

(72) Inventor: Michael Fraley, Casa Grande, AZ (US)

(73) Assignee: PanAridus, LLC, Casa Grande, AZ (US)

(*) Notice: Subject to any disclaimer, the term of this patent is extended or adjusted under 35 U.S.C. 154(b) by 0 days.

(21) Appl. No.: 14/400,323

(22) PCT Filed: May 7, 2013

(86) PCT No.: PCT/US2013/039989
§ 371 (c)(1),
(2) Date: Nov. 10, 2014

(87) PCT Pub. No.: WO2013/169809
PCT Pub. Date: Nov. 14, 2013

(65) Prior Publication Data
US 2015/0177129 A1    Jun. 25, 2015

Related U.S. Application Data

(60) Provisional application No. 61/644,343, filed on May 8, 2012.

(51) Int. Cl.
*G01J 5/02*        (2006.01)
*G01N 21/359*   (2014.01)
*G01N 21/84*     (2006.01)
(Continued)

(52) U.S. Cl.
CPC .............. *G01N 21/359* (2013.01); *G01N 21/84* (2013.01); *G01N 33/0098* (2013.01);
(Continued)

(58) Field of Classification Search
CPC .................................................. G01N 21/3563
USPC ....................................................... 250/339.01
See application file for complete search history.

(56) References Cited

U.S. PATENT DOCUMENTS 6,012,019 A    1/2000    Saby
6,072,576 A    6/2000    McDonald et al.
(Continued)

FOREIGN PATENT DOCUMENTS

WO    0071993 A1    11/2000

OTHER PUBLICATIONS

International Search Report and Written Opinion of the International Searching Authority for PCT/US2013/039989 dated Aug. 29, 2013.

*Primary Examiner* — David Porta
*Assistant Examiner* — Edwin Gunberg
(74) *Attorney, Agent, or Firm* — Rodney J. Fuller; Booth Udall Fuller, PLC

(57) ABSTRACT

A system and method for in-field near infrared spectroscopy (NIRS) analysis of rubber and resin concentrations a guayule plant is provided. The system includes a wagon or other vehicle with the NIRS device mounted on the wagon. A computer or processor electrically coupled to the NIRS device is also housed within an area or extension of the wagon. During measurement of a guayule plant in the field, a guayule plant covering is placed over the guayule plant and a light shield coupled to the NIRS device is inserted into an opening on the guayule plant covering. The NIRS device is configured to perform a reading of the guayule plant within the plant covering and communicate results of the reading to the computer. A calibration equation is then preferably applied to the guayule plant readings to produce the rubber and resin concentrations of the guayule plant.

19 Claims, 3 Drawing Sheets

(51) Int. Cl.
*G01N 33/00* (2006.01)

(52) U.S. Cl.
CPC ............... *G01N 2021/8466* (2013.01); *G01N 2201/0216* (2013.01); *G01N 2201/061* (2013.01); *G01N 2201/068* (2013.01); *G01N 2201/129* (2013.01)

(56) References Cited

U.S. PATENT DOCUMENTS

2005/0072935 A1* 4/2005 Lussier .................. 250/458.1
2010/0181496 A1 7/2010 Moise et al.

* cited by examiner

US 9,291,553 B2

SYSTEM AND APPARATUS FOR ANALYSIS OF A GUAYULE PLANT IN SITU

CROSS REFERENCE TO RELATED APPLICATIONS

This application is the U.S. National Stage of International Application No. PCT/US2013/039989, filed May 7, 2013, which claims the benefit of the filing date of U.S. Provisional Patent Application 61/644,343, entitled "System and Apparatus for Portable Use of a Near Infrared Spectroscopy Device" to Fraley which was filed on May 8, 2012, the contents of each of which are hereby incorporated by reference in their entireties.

FIELD OF THE INVENTION

This invention relates to portable apparatuses for measuring compositions of various materials.

BACKGROUND OF THE INVENTION

Near Infrared Spectroscopy (NIRS) is a method that provides multi-constituent analysis of a variety of matrices. Recently, NIRS has gained wide acceptance within many industries for raw material testing, product quality control, and process monitoring. Within the agricultural community, NIRS has wide use both in research (measuring quality parameters of individual plants or plats), and in quality control and measurement of many commodities.

The NIRS region of the electromagnetic spectrum is defined as the wavelength range of 780-2526 nm, which corresponds to the wave number range from 12820-3959 per cm. The most prominent absorption bands occurring in the NIRS region are related to overtones and combinations of fundamental vibrations of —CH, —NH, —OH (and —SH) functional groups. NIRS absorption bands are typically broad, overlapping, and 10-100 times weaker than their corresponding fundamental mid-IR absorption bands. These characteristics restrict sensitivity and require chemometric data processing to relate spectral information to sample properties. The low absorption coefficient, however, permits high penetration depth. With such broad, overlapping peaks, the spectra are very complex. It is often difficult to assign specific features of the spectrum to a specific chemical. Therefore, sophisticated software, using multivariate calibration techniques, is required. A calibration equation must be developed using careful sampling, analyzing in the best traditional method, and application of multivariate calibration techniques.

NIRS has previously been utilized to measure the composition of the guayule plant, particularly the rubber and resin concentrations. The guayule plant is well known as a producer of latex or rubber. Previously, rubber and resin concentrations in guayule were measured by slowly and carefully grinding portions of the plant into a very uniform substrate. This uniform substrate, often difficult to achieve, was then analyzed with NIRS focused on one or two individual wavelengths, rather than the entire NIR spectrum. Another previous NIRS-based measured of guayule required the guayule to be dried and finely ground.

SUMMARY

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar Thus, if a noun, term, or phrase is intended to be further characterized, specified, or narrowed in some way, then such noun, term, or phrase will expressly include additional adjectives, descriptive terms, or other modifiers in accordance with the normal precepts of English grammar Absent the use of such adjectives, descriptive terms, or modifiers, it is the intent that such nouns, terms, or phrases be given their plain, and ordinary English meaning to those skilled in the applicable arts as set forth above.

According to one aspect, a system for in-field near infrared analysis of a guayule plant in situ is contemplated. The system preferably comprises a wagon, a power source, a near infrared spectroscopy (NIRS) device, a light shield, and a guayule plant covering.

The wagon typically comprises a body frame and one or more wheels. The power source is typically coupled to the wagon. The NIRS device is typically positioned on the wagon, comprises a detector, is electrically coupled to the power source, and is configured to operably couple to a processor. The light shield is typically coupled to the NIRS device proximate the detector. The guayule plant covering is sized to fit over the guayule plant and comprises a hole extending through a sidewall. The guayule plant covering is configured to inhibit substantially all light from entering the guayule plant covering when the guayule plant covering is placed over a guayule plant and the light shield is adjacent the hole.

In one particular aspect, the light shield comprises a base shaped complimentary to a portion of the light covering and a head sized to fit at least partially within the hole of the guayule plant covering.

In another particular aspect, the processor is operably coupled to the NIRS device and configured to determine at least two percent moisture, a percent rubber, and a percent resin of the guayule plant in situ upon reception of NIRS readings from the NIRS device.

In a particular embodiment, the system further comprises an adjustable platform coupled to the body frame of the wagon, the adjustable platform being adjustable in at least one of a substantially horizontal direction or a substantially vertical direction.

The adjustable platform may be adjustable in the substantially vertical direction and the NIRS device may be mounted on a shelf slidably coupled to the adjustable platform such that the NIRS device is movable between a first position wherein the head of the light covering does not extend beyond the body frame and a second position wherein the head of the light covering extends at least partially beyond the body frame.

In a particular embodiment, the system further comprises an at least partially enclosed housing area coupled to the body frame, and the processor is housed within the partially enclosed housing area. The NIRS device may comprise up to a 30 centimeter diameter field of view, and the base of the light cover may abut a portion of the guayule plant covering and the head may be positioned at least partially within hole of the light covering.

A method of in-field analysis of rubber concentration and resin concentration of a guayule plant in situ using the system described above is also contemplated. According to one aspect, the method comprises placing the guayule plant covering over the guayule plant in situ, aligning the detector with the hole of the guayule plant covering, activating the NIRS device to determine a spectra reading of the guayule plant, communicating the spectra reading of the living guayule plant to the processor operably coupled to the NIRS device, and applying the spectra reading of the guayule plant to a calibration equation with the processor to determine the percent resin and percent rubber concentrations of the guayule plant.

For particular embodiments, aligning the detector with the hole of the guayule plant covering comprises moving the wagon to a position adjacent the guayule plant, adjusting a platform coupled to the wagon until a head of the light shield is aligned with the hole of the guayule plant covering, sliding a shelf coupled to the platform until the head of the light shield is at least partially within the hole of the guayule plant covering and a base of the light covering abuts a portion of the guayule plant covering.

In more particular embodiments, the method of in-field analysis of rubber concentration and resin concentration of a guayule plant in situ further comprises selecting a representative calibration sample set, the representative calibration sample set comprising a plurality of guayule plants, determining a reference rubber concentration and a reference resin concentration for each guayule plant of the representative calibration sample set with the NIRS device, determining the calibration equation using multivariate modeling to relate spectral variations of the reference rubber concentrations and the reference resin concentrations of the plurality of guayule plants of the representative calibration sample set, and validating the calibration equation by at least one of cross validation, set validation, and external validation.

In certain aspects, the representative calibration sample set comprises a first group of guayule plants selected after one summer of growth and an early winter, and a second group of plants selected after at least two winters of growth.

In particular embodiments, determining the reference rubber concentration and the reference resin concentration of the representative calibration sample set comprises placing the guayule plant covering over each guayule plant of the representative calibration set, inserting the head of the light covering at least partially into the hole extending through the guayule plant covering box, activating the NIRS device to determine the spectra reading of the each guayule plant of the representative calibration set, harvesting each guayule plant of the representative calibration set by collecting all biomass above approximately five centimeters of each guayule plant of the representative calibration set, drying each harvested guayule plant, removing leaves from each harvested guayule plant, and chipping each harvested guayule plant in a garden chipper, retrieving a subsample of each chipped guayule plant of the representative calibration set, drying each subsample, milling each subsample; and analyzing each subsample with an accelerated solvent extraction process. The processor is housed within a partially enclosed housing area of the wagon according to certain embodiments.

According to another aspect, a method of selecting preferred guayule plants for breeding is contemplated. The method typically comprises placing a guayule plant covering over a guayule plant in situ, the guayule plant covering comprising a hole extending through a sidewall, aligning a detector of a NIRS device positioned on a wagon with a hole extending through the guayule plant covering, activating the NIRS device to determine a spectra reading of the guayule plant in situ, communicating the spectra reading of the guayule plant to a processor operably coupled to the NIRS device, applying the spectra reading of the guayule plant to a calibration equation with the processor to determine a breeding attribute, the breeding attribute comprising at least one of a rubber concentration and a resin concentration of the guayule plant, determining whether the breeding attribute is preferred for breeding, and selecting the guayule plant for breeding if the breeding attribute is preferred.

In particular embodiments, aligning the detector with the hole of the guayule plant covering comprises moving the wagon to a position adjacent the guayule plant, adjusting a platform coupled to the wagon until a head of a light shield is aligned with the hole of the plant covering, sliding a shelf coupled to the platform until the head of the light shield is at least partially within the hole of the guayule plant covering and a base of the light covering abuts a portion of the guayule plant covering. The processor is housed within a partially enclosed housing area of the wagon according to certain embodiments.

The method of selecting preferred guayule plants for breeding may further comprise selecting a representative calibration sample set, the representative calibration sample set comprising a plurality of guayule plants, determining a reference rubber concentration and a reference resin concentration for each guayule plant of the representative calibration sample set with the NIRS device, determining the calibration equation using multivariate modeling to relate spectral variations of the reference rubber concentrations and the reference resin concentrations of the plurality of guayule plants of the representative calibration sample set, and validating the calibration equation by at least one of cross validation, set validation, and external validation.

In particular embodiments, the representative calibration sample set comprises a first group of guayule plants selected after one summer of growth and an early winter, and a second group of plants selected after at least two winters of growth. In more particular embodiments, determining the reference rubber concentration and the reference resin concentration of the representative calibration sample set comprises placing the guayule plant covering box over each guayule plant of the representative calibration set, inserting the head of the light shield at least partially into the hole extending through the guayule plant covering box, activating the NIRS device to determine the spectra reading of the each guayule plant of the representative calibration set, harvesting each guayule plant of the representative calibration set by collecting all biomass above approximately five centimeters of each guayule plant of the representative calibration set, drying each harvested guayule plant, removing leaves from each harvested guayule plant, and chipping each harvested guayule plant in a garden chipper, retrieving a subsample of each chipped guayule plant of the representative calibration set, drying each subsample, milling each subsample, and analyzing each subsample with an accelerated solvent extraction process.

In another aspect, a method of in-field analysis of rubber concentration and resin concentration of a living guayule plant is contemplated. The method typically comprises receiving, by a programmed computer system, a spectra reading of the living guayule from a NIRS device operably coupled to the programmed computer system, the NIRS device being mounted on a wagon positioned adjacent to the living guayule plant and the spectra reading determined by insertion of a head of a light shield into a guayule plant covering box covering the living guayule plant. The method also typically comprises applying the spectra reading of the living guayule plant to a calibration equation with the programmed computer system to determine the percent resin and percent rubber concentrations of the guayule plant.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Illustrative and exemplary embodiments of the invention are shown in the drawings in which.

Figure 1:
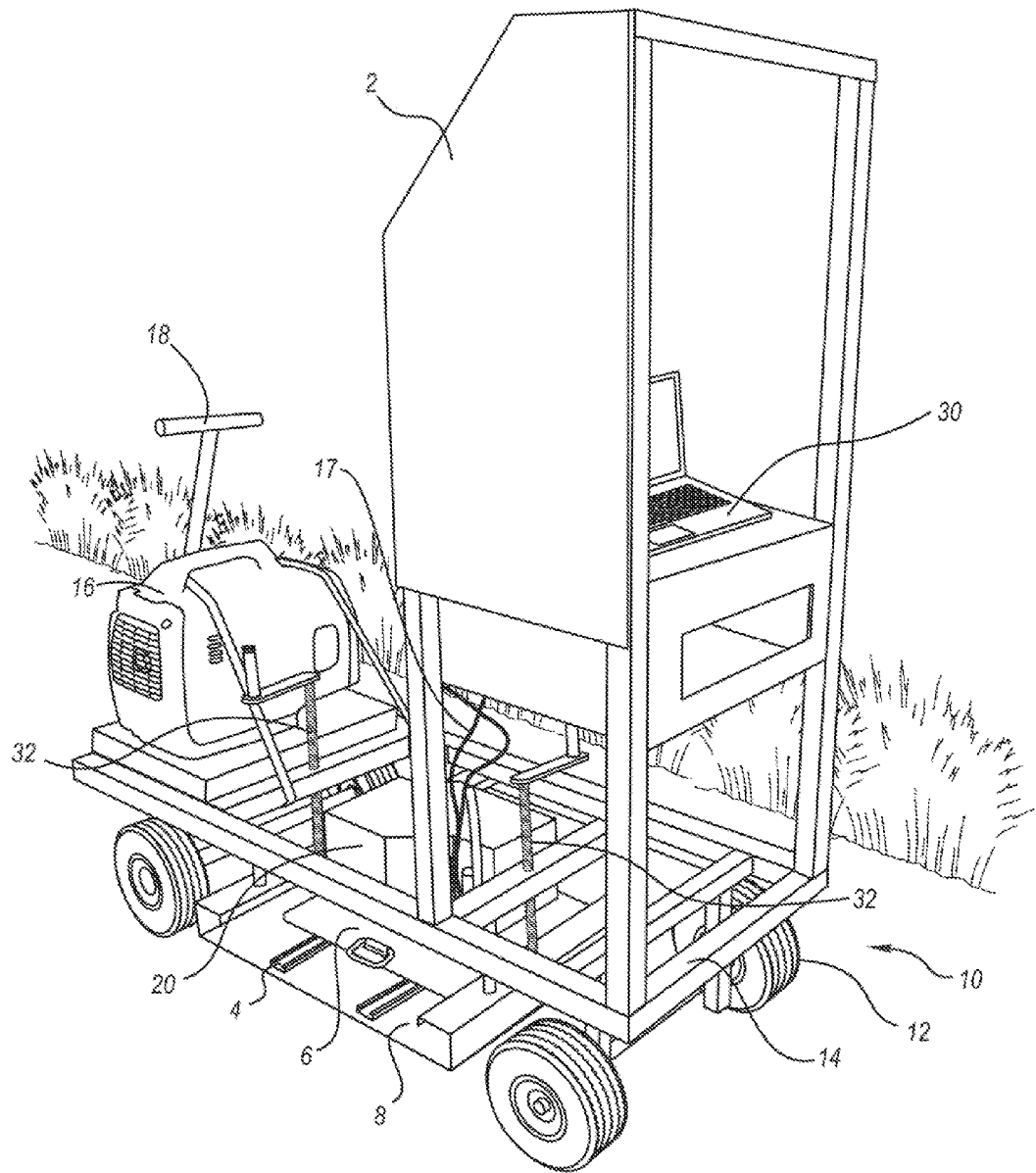
FIG. 1 depicts a perspective view of a portable NIRS device mounted to a wagon designed for in-field analysis of plants.

Elements and facts in the figures are illustrated for simplicity and have not necessarily been rendered according to any particular sequence or embodiment.

DETAILED DESCRIPTION OF THE INVENTION

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts.

Embodiments of the systems and apparatuses disclosed herein allow for the in-field compositional analysis of plants in situ utilizing a NIRS device 20. Compositional analysis of plants in situ does not require destruction of any part of the plant, but instead allows for compositional analysis of the plant in the plant's actual growing environment—such as a field. In a particular embodiment, the systems and apparatuses disclosed herein are specifically adapted for in situ compositional analysis of a guayule plant. It is contemplated, however, that the systems and apparatuses disclosed herein are adaptable to in situ compositional analysis of many plants. Reference to guayule plants is, therefore, provided by way of example and not limitation. When used in combination with appropriate software, embodiments of the systems and apparatuses provide an individual the results of the compositional analysis of the guayule plant within minutes, rather than hours or days. In a particular embodiment, the predicted percent rubber, percent resin, and percent moisture of the plant is reported on the computer 30 within approximately thirty seconds of activating the NIRS device for reading. Including set-up time for the day for the system, set-up time for each plant, and actual scan time, the average time to get a reading for each plant is approximately 90 to 120 seconds. In comparison, readings utilizing previously known systems typically take 90 to 120 minutes per plant. Furthermore, as previously referenced, the guayule plant is not damaged or wasted during the in-field analysis, and may, therefore, continue to grow for future use.

One or more embodiments of the systems disclosed herein comprise a NIRS device 20. The NIRS device may comprise any NIRS device known in the art. In a particular embodiment, the NIRS device 20 comprises a process analyzer, which provides real time information to the operator or other individuals. The process analyzer, according to one aspect, is specially designed for in-field use with a vehicle such as the wagon 10 described herein. For example, a specially developed process analyzer may comprise a field of view that is greater than a typical process analyzer. In a specific embodiment, the process analyzer comprises a spectrometer comprising up to a 30 cm diameter field of view and scanning over the 1.25 to 2.5 µm spectral range.

In an embodiment, the NIRS device 20 or spectrometer comprises a light source, a monochromator, sample presentation interface, and a detector 21. The light source in the NIRS device 20 typically comprises a tungsten halogen lamp. The detector may comprise silicon, lead sulfide, or indium gallium. In various embodiments, different designs of the NIRS device 20 allow for transmittance or reflectance.

The monochromator comprises a prism or other diffraction grating to separate light spatially. The light is focused through an exit slit to the detector 21. As the monochromator is adjusted to different wavelengths, the intensity of light of each wavelength over the range of interest may be measured over the course of the scan. The exit slit may comprise a limiting factor for the narrowness of the spectra being measured. Some embodiments of the NIRS device 20 utilize an interferometer instead of a monochromator. Such an embodiment is especially useful for certain wavelengths of light above 1000 nm. In utilizing an interferometer, the spectra are measured by the way different waves of light combine.

Embodiments comprising a laboratory analyzer are also contemplated. Sampling methods and procedures described throughout this document may be utilized with a laboratory analyzer. In this embodiment, the developed equation for the laboratory analyzer replaces the equation developed for use with the process analyzer, due to the difference in field of view between the laboratory and process analyzers. Moreover, although reference is made to components of one or more embodiments of an NIRS device 20, these references are by way of example and not for purposes of limitation. Therefore, the use of any NIRS device 20 previously known in the art and adapted for in-field use as described herein is also contemplated.

As shown in FIG. 1, a particular embodiment of the portable NIRS device for in-field use comprises at least a NIRS device 20 and a power source 16. The NIRS device 20 and power source 16 of the embodiment of FIG. 1 are mounted on a four-wheeled cart or wagon 10. In other embodiments, the NIRS device 20 is mounted on any type of cart, wagon, vehicle, and the like comprising any number of wheels 4. While the pictured embodiment does not comprise a motorized wagon or cart, other embodiments comprising a motorized cart, wagon or vehicle are contemplated.

In the embodiment shown in FIG. 1, the wagon 20 comprises a body frame 14, a partially enclosed housing area, and a handle 18. The body frame 14 may comprise any configuration that allows for transportation of the NIRS device 20. The body frame 14 of the embodiment shown in FIG. 1 is configured to couple to four wheels 12 and comprises an opening in the body frame 14 that allows for controlled vertical movement of the NIRS device through the opening. The handle 18 may comprise any handle or other gripping element that allows a user to pull or push the wagon 10.

Although not required in each embodiment, the embodiment depicted in FIG. 1 comprises a partially enclosed housing area 2. The housing area 2 typically comprises one or more sidewalls positioned to create a cavity within the housing. The cavity is sized to house and shade one or more computers 30 or other electronic devices, thus allowing for more efficient use of the computer 30.

The power source 16 shown in FIG. 1 comprises a gas-powered generator, but other power sources 16 are also contemplated and suitable. The NIRS device 20 is typically electrically coupled to the power source 16. In other embodiments, the NIRS device 20 may be electrically coupled to a variety of power sources. For example, different embodiments are powered by the motor of the wagon 10 or vehicle, a rechargeable battery mounted to the wagon 10, or an electrical cord running from the wagon 10 to a power source. The power source 16 is also typically configured to provide power to a computer 30 housed within the partially enclosed housing area 2. According to one aspect, one or more cords 17 electrically couple the power source 16 to the NIRS device and the computer 30.

An embodiment of the wagon 10 further comprises a platform 8 approximately central to the wagon and coupled to the NIRS device 20. According to various aspects, the platform 8 comprises an adjustable platform 8 that is adjustable in at least one of a vertical direction and a horizontal direction. In the embodiment depicted in FIG. 1, the platform 8 is adjustable in a vertical direction that allows a user to raise or lower the height of the NIRS device 20 positioned on the platform 8. Adjusting the platform in a substantially vertical direction allows a user to adjust the NIRS device according to the size of the guayule plant or according to the environment adjacent the guayule plant. Raising and lowering of the platform may be accomplished with a hydraulic system, a rotatable screw mount, and the like. In a particular embodiment, the platform 8 is adjusted with a rotatable screw mount 32 such that the field of view is 15 centimeters from ground level in the center of the plant.

In one or more embodiments, the platform 8 further comprises at least one track 4 configured to a guide a shelf 6 or other member. In the embodiment depicted in FIG. 1, the NIRS device 20 rests or is otherwise mounted on a shelf 6 that is slidably engaged with two tracks 4 on the platform 8. The shelf 6 may be slidably engaged or otherwise slidably coupled to the tracks 4 according to any mechanism known in the art. By providing a shelf 6 slidably coupled to the platform 8, the NIRS device 20 is movable between a first position wherein a head 22 of a light shield 25 does not extend beyond the body frame 12 (shown in FIG. 1), and a second position wherein the head 22 extends beyond the body frame 12 (shown in FIGS. 2 and 3). Such movement allows the NIRS device 20 to be slid closer to the guayule plant for analysis. In a particular embodiment, the shelf 6 extends about 20-30.5 centimeters beyond the edge of the platform 8. In other embodiments, the shelf 6 and tracks 4 are configured such that the track extends more or less than about 20-30.5 centimeters beyond the edge of the platform. Typically, the tracks 4 are parallel to the axels of the wheels 12 on the wagon 10. In some embodiments, however, the tracks 4 may be perpendicular or in any direction relative to the axels of the wheels 12 of the wagon 10.

One or more embodiments further comprise a computer 30 or other processor electrically coupled to the NIRS device 20. The computer 30 may comprise a database of previous NIRS compositional analysis of guayule or other plants. The computer 30 further comprises a display, graphical user interface, keyboard, or any other instruments known in the art according a preferred embodiment. In particular embodiments, the computer 30 comprises a laptop or other portable computer or tablet device with Ethernet (LAN) or any other network connectivity capabilities. A software interface may also be utilized between the NIRS device 20, the computer 30, and the user, allowing the user to view and transmit results, control data, review measurements, and the like.

Figure 2:
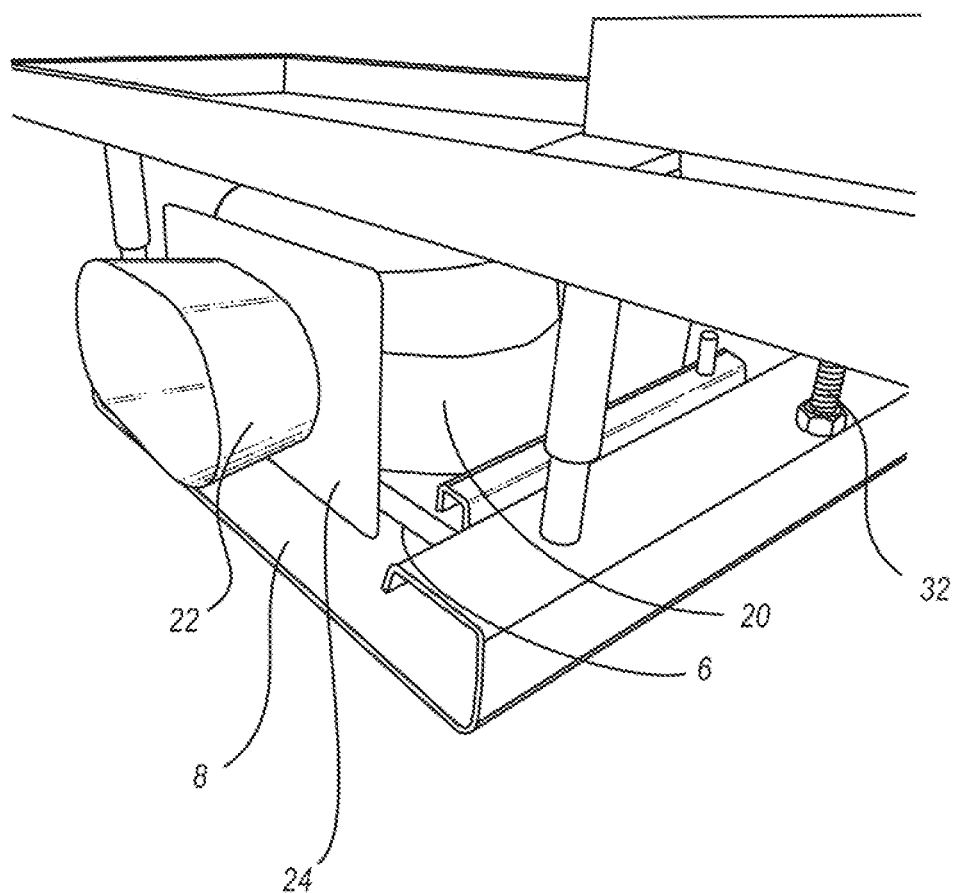
FIG. 2 shows a partial perspective view of the NIRS device, platform, and light shield on the wagon designed for in-field analysis of plants.

FIG. 2 depicts a partial side perspective view of the body frame 14, platform 8, shelf 6 of an embodiment of a wagon 10, as well as a NIRS device 20 positioned thereon. As shown in FIG. 2, one or more embodiments of the system or method comprise a light shield 25 coupled to the NIRS device 20. According to various aspects contemplated, the light shield 25 may comprise any configuration that prevent light from entering the guayule plant covering 40 when the detector 21 is aligned with hole 42 of the plant covering 40. For example, the light covering 25 may comprise a hollow tube, a hollow coned shaped extension, a malleable wall surrounding the detector 21, an adjustable wall surrounding the detector 21, and the like. In the specific embodiment shown in FIG. 2, the light shield comprises a head 22 and a base 24. The head 22 is typically shaped and sized to fit at least partially into the hole 42. In the specific embodiment depicted in FIG. 2, the head 22 is substantially elliptical in shape. As depicted, the head 22 may increase in size towards the opening opposite the base 24. In other embodiments, the head 22 is sized or otherwise configured in any shape that complements the hole 42 on the plant covering 40. In an embodiment, the head 22 comprises a 17.5 centimeter by 22.5 centimeter elliptical wall.

In one or more embodiments, a base 24 of the light shield 25 is coupled to the housing of the NIRS device 20 to assist in correctly positioning the detector 21 on the NIRS device 20. For example, the base 24 may contact an edge of the plant covering box 40 or abut the plant covering box 40 itself to correctly position the probe relative to the plant covered by the plant covering box 40. As a result, a constant distance is maintained between the probe and the plant during sampling of one plant, and also from one plant sample to another plant sample. The base 24 is typically shaped to complement at least a portion of the plant covering 40 proximate the hole 42. In the specific embodiment depicted in FIG. 2, the base 24 is substantially planar to complement the planar side wall 46 of the plant covering 42. According to one aspect, the base 24 is positioned between the NIRS device 20 housing and the head 22 of the light shield 25.

The base 24 and/or the head 22 of the light shield 25 may be comprised of a variety of materials, such as but not limited to metals such as aluminum or steel compounds. In a particular embodiment, the base 24 and/or head 22 of the light shield 25 comprise a material identical to the material of the plant covering box 40.

Figure 3:
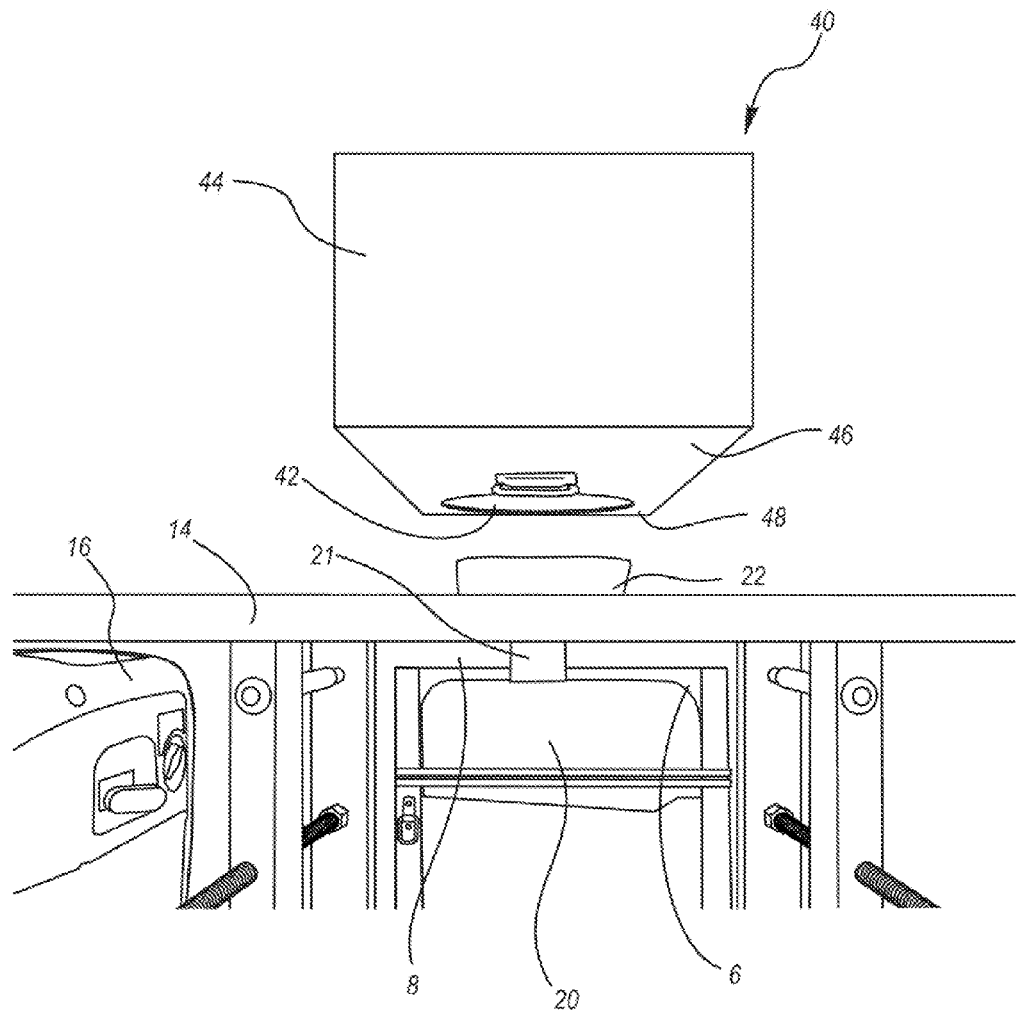
FIG. 3 shows a partial top view of the NIRS device mounted on the wagon and the plant covering box for in-field analysis of plants.

FIG. 3 depicts a top view of a portion of the body frame 14 of the wagon 10, the NIRS device 20, the head 22 of the light shield 25, and a plant covering 40. As previously described, the NIRS device 20 may be slid along the tracks 4 to a second position closer to the plant and/or plant covering 40. In one particular embodiment, the plant covering 40 comprises one open first end 48, a closed second end 44 opposite the open first end 48, and one or more sidewalls 46 extending between the open first end 48 and the closed second end 44. The plant covering 40 further comprises a hole 42, opening, or other void sized to allow at least a portion of the head 22 of the light shield 25 to extend through the opening. The hole 42 may be positioned on a sidewall 46 or a top end 44. In a particular embodiment, the plant covering 40 comprises a reflective box made of aluminum or galvanized steel. In other embodiments, the plant covering 40 may be made of any metal or non-NIRS interfering material that allows the plant to be covered and eliminate or inhibit sunlight or other light from entering into the box when the head 22 of the light shield is engaged with or otherwise at least partially extending through the hole 42.

For example, any material lined with aluminum foil may be suitable from a spectral point of view.

Different sizes and/or shapes of plant coverings 40 may be utilized in plants of different age and/or size. In a particular aspect, a plant covering 40 comprises a box with the dimensions of about 46-86 centimeters tall, e.g., 61 centimeters tall; about 30.5-61 centimeters wide, e.g., 40 centimeters wide; and about 35-71 centimeters deep, e.g., 53 centimeters deep. In such an embodiment, the 40 centimeters wide face comprises the elliptical hole 42 that matches the head 22 of the light shield 25 on the NIRS device 22. In another aspect, the plant covering 40 comprises a box with the dimensions of 61 centimeters tall, 30.5 centimeters wide, and 46 centimeter deep. In still another aspect, the plant covering 40 comprises a box with the dimensions of 61 centimeter wide, 76 centimeters tall, and 61 centimeters deep. In other embodiments, the plant covering 40 comprises any shape or configuration that allows the plant covering 40 to be placed over the plant, such as but not limited to a bag-like configuration, a spherical configuration, a hinged box, a collapsible box, and the like.

When the plant is within the plant covering 40 and the head 22 of the light shield 25 is at least partially inserted into the hole 42 of the plant covering 40, substantially all sunlight or other light is prevented or inhibited from entering the plant covering. The NIRS device 20 may then be activated to measure various compositional attributes of the guayule or other plant.

A system and method for measuring various properties of a plant with the portable NIRS device 20 is also contemplated and described herein. The NIRS device 20 in combination with the calibration equation has a variety of implementations. For example, within agricultural research, the system and methods may be applied to select preferred plants for breeding, variety characterization, and agronomic studies. For production purposes, fields of guayule plants can be tracked to predict the percent rubber from fields that will soon be harvested.

Plant breeding in general is utilized to develop genetically superior varieties of plants based on one or more breeding attributes. In a particular embodiment, one or more of the systems and apparatuses disclosed herein are used to select parent plants that are genetically superior for accumulating rubber and/or resin. Because the compositional analysis described herein is in situ, the sampling is nondestructive and seed can be harvested from the best guayule plants quickly. According to another aspect of plant breeding, variety characterization is utilized to monitor the progress of breeding attributes. Therefore, the best new varieties developed using plant breeding are efficiently compared to standard checks to characterize the advancements made in rubber production. Use of one or more of the systems and apparatuses described herein allows for this characterization without harm to the subject plants.

Also contemplated in this disclosure is a method for selecting guayule plants in situ for breeding purposes. Such a method typically comprises activating a NIRS device to perform a spectra reading of a first guayule plant in situ. The NIRS device utilized in the method may comprise any NIRS device known in the art and is not limited to any of the NIRS devices disclosed herein. Furthermore, performing the spectra reading of the guayule plant in situ with the NIRS device may be accomplished with or without the wagon described herein. For example, in particular embodiments, a handheld NIRS device known in the art may also be configured to determine a spectra reading of the one or more guayule plants in situ. The method typically further comprises applying the spectra reading of the first guayule plant in situ to a calibration equation to determine the percent rubber concentration and the percent resin concentration of the first guayule plant. The method may further comprise activating the NIRS device to a perform a spectra reading of at least a second guayule plant and applying the spectra reading to the calibration equation to determine the percent resin concentration and the percent rubber concentration of the at least second guayule plant. Embodiments of the method may comprise determining a spectra reading of any number of guayule plants. The method further comprises determining whether the first or the at least second guayule plant comprises higher percent resin concentration and/or percent rubber concentration, and then selecting the guayule plant with the higher percent resin concentration and/or percent rubber concentration as the breeding plant.

According to another aspect, one or more of the systems and apparatuses disclosed herein are utilized in agronomic applications. For example, the NIRS device 20 may be used to characterize the rubber and/or resin production of guayule plants that have received various treatments, such as but not limited to different levels of spacing, fertilizer, irrigation, planting date, and the like.

In particular, a system and method for measuring at least one of the percent moisture, percent rubber, and percent resin of a guayule plant with the portable NIRS device 20 is contemplated. Particular embodiments of the system and method may comprise variations or combinations the following: selecting a representative calibration sample set; acquiring appropriate spectra; determining a reference value; multivariate modeling relating the spectral variations to the reference values; validating the model by cross validation, set validation, or external validation; positioning the NIRS device 20 proximate a plant; placing the plant covering 40 over the plant; aligning or inserting a head 22 of a light shield 25 coupled to the NIRS device 20 within the hole 42 on the plant covering 40 such that substantially all light is prevented or inhibited from entering the plant covering 40 through the hole 42; activating the NIRS device 20; applying the spectra reading of the guayule plant to a calibration equation with the processor determine the percent resin and percent rubber concentrations of the guayule plant; and displaying the plant measurements on a computer 30 or processor display.

Guayule plants typically have rubber in the bark of the plant, but not in the wood. NIRS technology was selected as a potential technology for rubber measurement in the guayule plant because NIRS wavelengths typically have excellent penetration into a material. Percent rubber in the bark of the guayule plant may, however, vary in different parts or locations on the plant. Therefore, a large field view provides a more accurate prediction of rubber concentration in a growing, un-harvested plant and an NIRS device 20 with a wider field of view may be preferred. In a particular embodiment, a NIRS device with about a 12-30 centimeter field, more preferably 16-26 centimeter field, e.g., about 20 centimeter field of view, is utilized to develop a calibration equation. Such a device preferably measures absorbance in the 4 to 8000 waves per centime portion of the spectra.

Selecting a representative calibration sample set may comprise selecting plants of different ages. For example, guayule typically makes rubber in the bark in the winter dormant season. Therefore, an embodiment of the system further comprises sampling plants after one summer of growth and after a late fall or early winter of producing rubber. In an embodiment, the time is measured relative to transplantation of the plant. Mature plants that have gone through at least two winters may also be selected for sampling. Beyond different age groups, selecting a representative calibration sample set further comprises selecting plants from differing morphologies with the age groups and/or from differing locations according to a particular embodiment.

In one aspect, at least 250 or 300 plant samples are required to develop the initial calibration equation. Plants may be selected based on previous knowledge of expected rubber levels based on age, morphology, and location, or any other factors that achieve a desired representation of expected compositional diversity of guayule plants. The desired representation, therefore, typically includes plants representing high and lubber rubber types from both immature and mature plants, as well as from all different plant types.

In another aspect, additional plant sampling beyond the at least 250 or 300 plant samples is conducted to create a more robust sample size. Increasing the sample size may increase the accuracy of the equation. Selection of additional plants for sampling is based on not only the previously mentioned criteria, but also based on plants comprising a specifically desired or otherwise unique spectra. Spectra of plant that are uniquely different from plants already in the reference set may be targeted. In a particular embodiment, software is utilized to analyze how well the spectra from a particular plant fits into the current equation. Accordingly, a plant that does not fit well within the equation is commonly chosen or targeted to further expand the reliability and usefulness of the equation.

According to one aspect, determining a reference value comprises performing spectra readings with the NIRS device 20 on each plant described above. The reference value may comprise a reference rubber concentration, a reference resin concentration, a reference percent moisture, or any combination thereof. In determining the reference value, the plant covering box 30 is typically placed over the plant on which the spectra reading is being performed to eliminate or inhibit substantially all sunlight during reading. The head 22 of the light shield 25 is then inserted into the hole 42 on the plant covering 40, and each plant is measured at least once while the head 42 of the light shield 25 is within the plant covering 40. In various embodiments, the field of view may be centered at a uniform height above the ground to improve consistency of the readings. In a particular embodiment, the field of view is centered 15 centimeters above ground level in the center of the plant. As previously noted, the adjustable platform 8 may be adjusted to ensure that the field of view is at a consistent height from the ground level for the plurality of samples.

After performing the NIRS reading on each plant, a subsample is typically taken to measure the moisture levels of the plant. This subsample of the plant may be weighed before and after drying to predict percent moisture in the whole plant. The subsample may then be dried for a selected period of time, at an ambient temperature and humidity. In a particular embodiment, a preferred ambient temperature is between 10 and 20° Celsius. The subsamples may also or alternatively be dried for selected period of time at a selected temperature. In a particular embodiment, the subsample is dried for several days at ambient temperature and humidity, then two days and 80° C. before a final weight was taken.

In one preferred embodiment, determining the reference value further comprises harvesting each plant previously read by the NIRS device (described above). All biomass from above 5 centimeters above the grown is harvested, stored, and dried according to an aspect. Drying of the harvested plant may be at an ambient temperature and humidity, or may alternatively be at proscribed temperature and humidity. In an embodiment, the harvested plants are dried until leaves are easily removed from the branches. The branches are then passed through a garden chipper or other similar device at least once. To prevent cross-contamination, the garden chipper is typically cleaned between samples.

The chipped branches from each sample are then individually mixed and sub-sampled in a particular embodiment. The subsample of chips may then be dried before a milling process that finely grinds the subsample. Drying of the subsample typically takes place in a drying oven at 40 degrees Celsius. According to one aspect, the milling process is completed or carried out utilizing a laboratory ball mill, such as the Retsch MM 301. Each subsample is then analyzed in a laboratory with assistance of an accelerated solvent extraction machine (ASE). Standard operating procedures for extracting resin and rubber from guayule may be used in the laboratory. For purposes of reliability, three replicates per plant are typically analyzed us ASE. Finally, analysis results in a reported percent resin and a percent rubber for each plant.

The resin, rubber, and percent moisture for each plant are then utilized in a principal component analysis and multivariate techniques to develop a calibration equation. The calibration equation may then be programmed into a processor, computer, etc., for use in the field.

In the field, percent moisture, resin, and rubber are typically measured by inserting NIRS readings of a particular plant into the calibration equation. NIRS readings of a particular plant in the field may be achieved as previously described, that is, inserting the aligning the detector 21 of the NIRS device with the hole 42 of the NIRS device 20 and activating the NIRS device 20. Results of the NIRS spectral readings of the particular plant in the field are then transmitted to the computer 30 or processor, which applies the calibration equation to the readings of the particular plant in the field. The computer 30 or processor interface finally shows the predicted percent resin, percent rubber, and percent moisture.

Embodiments of the systems and methods presented herein are advantageous to previous systems and methods for measuring percent moisture, percent rubber, and percent resin in guayule plants. Whereas previous systems and methods required complete destruction of the guayule plant and time consuming methods of analysis, embodiments presented herein allow these measurements to be completed on a living plant in a matter of minutes.

Also contemplated herein is a computer system comprising one or more processors and one or more databases. According to various aspects, the computer system is configured to receive the calibration equation described herein. The computer system is further configured to operatively couple to the NIRS device 20 and receive a spectra reading of a guayule plant in situ. Upon receipt of the spectra reading from the NIRS device, the computer system is configured to apply the spectra reading to the calibration equation to determine at least one of the percent moisture, the percent resin, or the percent rubber of the plant. Once determined, the computer system may display the percent moisture, percent resin, and/or the percent rubber. The computer system may also store the determined concentrations and/or communicate the determined concentrations to other computers. The determined concentrations are, in a particular embodiment, reported as a predicted percent resin (dry defoliated basis), a predicted percent rubber (dry defoliated basis), and a percent moisture.

Having herein set forth the various embodiments of the present invention, it is anticipated that suitable modifications can be made thereto which will nonetheless remain within the scope of the invention. The invention shall therefore only be construed in accordance with the following claims below.

What is claimed is:

1. A system for in-field near infrared analysis of a guayule plant in situ, comprising:
   a wagon comprising a body frame and one or more wheels;
   a near infrared spectroscopy (NIRS) device positioned on the wagon and comprising a detector operably coupled to a processor, the NIRS device being configured to determine a spectra reading of the guayule plant and communicate the spectra reading of the guayule plant to the processor, the processor being configured to apply the spectra reading of the guayule plant to a calibration equation to determine the percent resin and percent rubber concentrations of the guayule plant, wherein the calibration equation was determined using multivariate modeling;
   a light shield coupled to the NIRS device proximate the detector; and
   a guayule plant covering sized to fit substantially over the guayule plant, the guayule plant covering comprising a hole extending through a sidewall.

2. The system of claim 1, wherein the light shield comprises a base shaped complimentary to a portion of the light covering and a head sized to fit at least partially within the hole of the guayule plant covering.

3. The system of claim 2, further comprising an adjustable platform coupled to the body frame of the wagon, the adjustable platform being adjustable in at least one of a substantially horizontal direction or a substantially vertical direction.

4. The system of claim 3, wherein the adjustable platform is adjustable in the substantially vertical direction and the NIRS device is mounted on a shelf slidably coupled to the adjustable platform such that NIRS device is movable between a first position wherein the head of the light covering does not extend beyond the body frame and a second position wherein the head of the light covering extends at least partially beyond the body frame.

5. The system of claim 4, further comprising an at least partially enclosed housing area coupled to the body frame, wherein the processor is housed within the partially enclosed housing area.

6. The system of claim 5, wherein the NIRS device comprises a field of view of less than or equal to 30 centimeters in diameter.

7. The system of claim 2, wherein the base of the light shield is abutting a portion of the guayule plant covering and the head is at least partially within the hole of the light shield.

8. A method of in-field analysis of rubber concentration and resin concentration of a guayule plant in situ using the system of claim 1, the method comprising:
   placing the guayule plant covering over the guayule plant in situ;
   aligning the detector with the hole of the guayule plant covering;
   activating the NIRS device to determine a spectra reading of the guayule plant;
   communicating the spectra reading of the living guayule plant to the processor operably coupled to the NIRS device; and
   applying the spectra reading of the guayule plant to a calibration equation with the processor to determine the percent resin and percent rubber concentrations of the guayule plant, wherein the calibration equation was determined using multivariate modeling.

9. The method of claim 8, wherein aligning the detector with the hole of the guayule plant covering comprises:
   moving the wagon to a position adjacent the guayule plant;
   adjusting a platform coupled to the wagon until a head of the light shield is aligned with the hole of the guayule plant covering;
   sliding a shelf coupled to the platform until the head of the light shield is at least partially within the hole of the guayule plant covering and a base of the light covering abuts a portion of the guayule plant covering.

10. The method of claim 9, further comprising:
    selecting a representative calibration sample set, the representative calibration sample set comprising a plurality of guayule plants;
    determining a reference rubber concentration and a reference resin concentration for each guayule plant of the representative calibration sample set with the NIRS device;
    determining the calibration equation using multivariate modeling to relate spectral variations of the reference rubber concentrations and the reference resin concentrations of the plurality of guayule plants of the representative calibration sample set; and
    validating the calibration equation by at least one of cross validation, set validation, and external validation.

11. The method of claim 10, wherein the representative calibration sample set comprises a first group of guayule plants selected after one summer of growth and an early winter, and a second group of plants selected after at least two winters of growth.

12. The method of claim 9, wherein determining the reference rubber concentration and the reference resin concentration of the representative calibration sample set comprises:
    placing the guayule plant covering over each guayule plant of the representative calibration set;
    inserting the head of the light covering at least partially into the hole extending through the guayule plant covering box;
    activating the NIRS device to determine the spectra reading of the each guayule plant of the representative calibration set;
    harvesting each guayule plant of the representative calibration set by collecting all biomass above approximately five centimeters of each guayule plant of the representative calibration set, drying each harvested guayule plant, removing leaves from each harvested guayule plant, and chipping each harvested guayule plant in a garden chipper;
    retrieving a subsample of each chipped guayule plant of the representative calibration set;
    drying each subsample;
    milling each subsample; and
    analyzing each subsample with an accelerated solvent extraction process.

13. The method of claim 8, wherein the processor is housed within a partially enclosed housing area of the wagon.

14. A method of selecting preferred guayule plants for breeding, comprising
    placing a guayule plant covering over a guayule plant in situ, the guayule plant covering comprising a hole extending through a sidewall;
    aligning a detector of a NIRS device positioned on a wagon with a hole extending through the guayule plant covering;
    activating the NIRS device to determine a spectra reading of the guayule plant in situ;

communicating the spectra reading of the guayule plant to a processor operably coupled to the NIRS device;

applying the spectra reading of the guayule plant to a calibration equation with the processor to determine a breeding attribute, the breeding attribute comprising at least one of a rubber concentration and a resin concentration of the guayule plant, wherein the calibration equation was determined using multivariate modeling;

determining whether the breeding attribute is preferred for breeding; and selecting the guayule plant for breeding if the breeding attribute is preferred.

15. The method of claim 14, wherein aligning the detector with the hole of the guayule plant covering comprises:

moving the wagon to a position adjacent the guayule plant;

adjusting a platform coupled to the wagon until a head of a light shield is aligned with the hole of the plant covering;

sliding a shelf coupled to the platform until the head of the light shield is at least partially within the hole of the guayule plant covering and a base of the light covering abuts a portion of the guayule plant covering.

16. The method of claim 15, wherein the processor is housed within a partially enclosed housing area of the wagon.

17. The method of claim 16, further comprising:

selecting a representative calibration sample set, the representative calibration sample set comprising a plurality of guayule plants;

determining a reference rubber concentration and a reference resin concentration for each guayule plant of the representative calibration sample set with the NIRS device;

determining the calibration equation using multivariate modeling to relate spectral variations of the reference rubber concentrations and the reference resin concentrations of the plurality of guayule plants of the representative calibration sample set; and validating the calibration equation by at least one of cross validation, set validation, and external validation.

18. The method of claim 17, wherein the representative calibration sample set comprises a first group of guayule plants selected after one summer of growth and an early winter, and a second group of plants selected after at least two winters of growth.

19. The method of claim 17, wherein determining the reference rubber concentration and the reference resin concentration of the representative calibration sample set comprises:

placing the guayule plant covering box over each guayule plant of the representative calibration set;

inserting the head of the light shield at least partially into the hole extending through the guayule plant covering box;

activating the NIRS device to determine the spectra reading of the each guayule plant of the representative calibration set;

harvesting each guayule plant of the representative calibration set by collecting all biomass above approximately five centimeters of each guayule plant of the representative calibration set, drying each harvested guayule plant, removing leaves from each harvested guayule plant, and chipping each harvested guayule plant in a garden chipper;

retrieving a subsample of each chipped guayule plant of the representative calibration set;

drying each subsample;

milling each subsample; and analyzing each subsample with an accelerated solvent extraction process.

* * * * *